United States Patent
Bonrath et al.

(10) Patent No.: US 9,957,228 B2
(45) Date of Patent: May 1, 2018

(54) PROCESS OF PRODUCTION OF 7,8-DIHYDRO-C15-ALDEHYDE

(71) Applicant: DSM IP ASSETS B.V., Heerlen (NL)

(72) Inventors: Werner Bonrath, Kaiseraugst (CH); Jan Schuetz, Kaiseraugst (CH); Thomas Netscher, Kaiseraugst (CH); Bettina Wuestenberg, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days. days.

(21) Appl. No.: 15/518,097

(22) PCT Filed: Oct. 15, 2015

(86) PCT No.: PCT/EP2015/073867
§ 371 (c)(1),
(2) Date: Apr. 10, 2017

(87) PCT Pub. No.: WO2016/059150
PCT Pub. Date: Apr. 21, 2016

(65) Prior Publication Data
US 2017/0313654 A1    Nov. 2, 2017

(30) Foreign Application Priority Data

Oct. 16, 2014 (EP) .................................. 14189265

(51) Int. Cl.
| | | |
|---|---|---|
| C07C 45/00 | (2006.01) | |
| C07C 403/14 | (2006.01) | |
| C07C 45/51 | (2006.01) | |
| C07C 47/21 | (2006.01) | |
| C07C 47/225 | (2006.01) | |
| C07C 13/20 | (2006.01) | |

(52) U.S. Cl.
CPC ............ *C07C 403/14* (2013.01); *C07C 13/20* (2013.01); *C07C 45/512* (2013.01); *C07C 47/21* (2013.01); *C07C 47/225* (2013.01); *C07C 2523/00* (2013.01); *C07C 2601/16* (2017.05)

(58) Field of Classification Search
CPC ............................ C07C 45/512; C07C 403/14
USPC ........................................................... 568/446
See application file for complete search history.

(56) References Cited

U.S. PATENT DOCUMENTS 3,994,936 A    11/1976    Andrews et al.

FOREIGN PATENT DOCUMENTS

JP    38-2269    3/1963

OTHER PUBLICATIONS

International Search Report for PCT/EP2015/073867, dated Dec. 15, 2015, 4 pages.
Written Opinion of the ISA for PCT/EP2015/073867, dated Dec. 15, 2015, 7 pages.
Nakatsubo et al., "Synthesis and stereochemistry of latia luciferin", Tetrahedron Letters, vol. 11, No. 5, Jan. 1970, pp. 381-382.
Kojima et al., "Bioluminescence activity of Latia luciferin analogs", Tetrahedron Letters, vol. 41, nol. 22, Jun. 2000, pp. 4409-4413.
Fontán et al., "Stereoselective Synthesis by Olefin Metathesis and Characterization of [eta]-Carotene (7,8,7',8'-tetrahydro-[beta],[beta]-carotene)", Journal of Natural Products, vol. 75, No. 5, May 25, 2012, pp. 975-979.
Semenovskii et al., "Cyclization of dehydronerolidol acetate—A route for the synthesis of cyclic isoprenoids", Bulletin of the Academy of Sciences of the USSR; Division of Chemical Sciences, vol. 16, No. 5, May 1967, pp. 1107-1109.
Douglas et al., "The Meyer-Schuster rearrangement for the synthesis of [alpha],[beta]-unsaturated carbonyl compounds", Organic & Biomolecular Chemistry, vol. 7, No. 20, Jan. 2009, p. 4149.

*Primary Examiner* — Sikarl A Witherspoon
(74) *Attorney, Agent, or Firm* — Nixon & Vanderhye P.C.

(57) ABSTRACT

The present invention relates to a new method to produce 7,8-dihydro-$C_{15}$-aldehyde.

14 Claims, No Drawings

PROCESS OF PRODUCTION OF 7,8-DIHYDRO-C15-ALDEHYDE

This application is the U.S. national phase of International Application No. PCT/EP2015/073867 filed 15 Oct. 2015, which designated the U.S. and claims priority to EP Patent Application No. 14189265.3 filed 16 Oct. 2014, the entire contents of each of which are hereby incorporated by reference.

The present invention relates to a new method to produce 7,8-dihydro-$C_{15}$-aldehyde.

7,8-dihydro-$C_{15}$-aldehyde is the compound of formula (I)

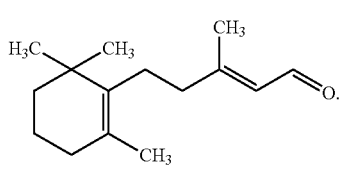

(I)

The IUPAC name of the 7,8-dihydro-$C_{15}$-aldehyde is 3-methyl-5-(2',6',6'-trimethylcyclohex-1'-en-1'-yl)pent-2-enal.

In the context of the present invention the compound of formula (I) is representing and covering all isomeric forms (E and Z forms).

The 7,8-dihydro-$C_{15}$-aldehyde, can be used for example as an intermediate in the production of 7,8,7',8'-tetrahydro-β-carotene, which is the compound of formula (II):

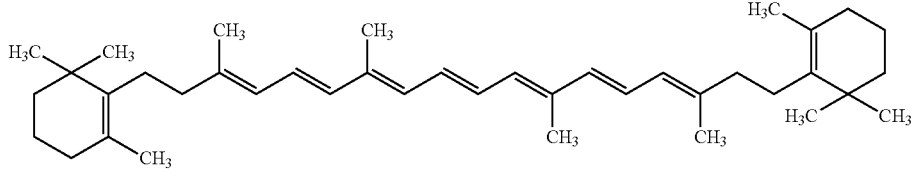

(II)

Due to the importance of the 7,8-dihydro-$C_{15}$-aldehyde new methods of its production are always of interest.

It is known from the prior art (i.e. from J. Nat. Prod. 2012, 75, 975-979) to produce 7,8-dihydro-$C_{15}$-aldehyde by a 3 step procedure starting from dihydro-β-ionone (compound of formula (III)). The following scheme illustrates this process:

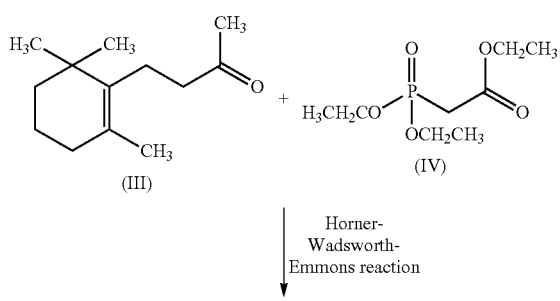

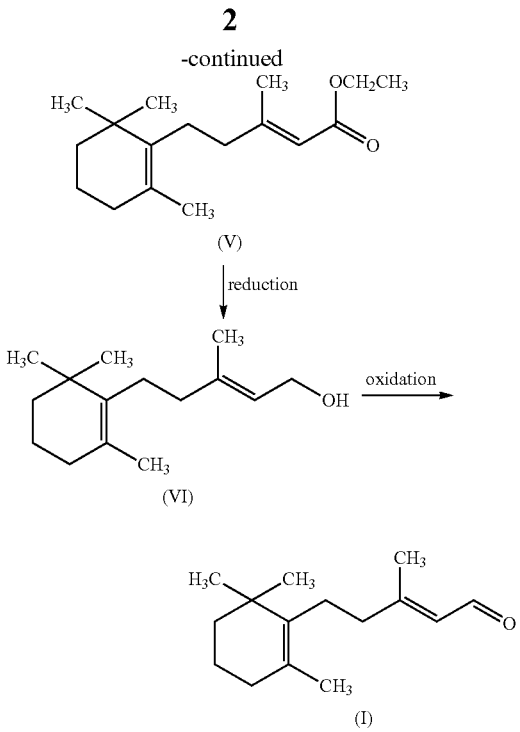

Now, it was found that it is possible to produce the 7,8-dihydro-C15-aldehyde by a two step-process, whereby the yield is excellent.

The present invention relates to a process for the production of a compound of formula (I) (7,8-dihydro-$C_{15}$-aldehyde or 3-methyl-5-(2',6',6'-trimethylcyclohex-1'-en-1'-yl)pent-2-enal) wherein
the first step is an ethynylation of dihydro-β-ionone and
the second step is a metal-based catalyzed rearrangement.

The process according to the present invention can be represented by the following reaction scheme:

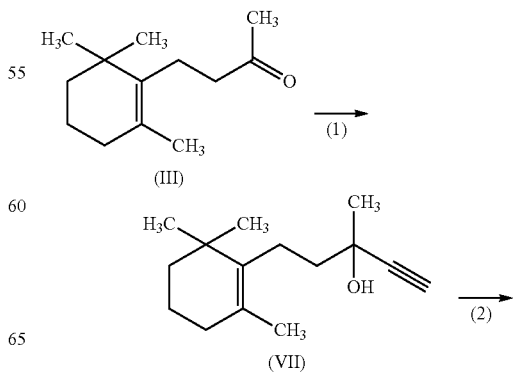

-continued

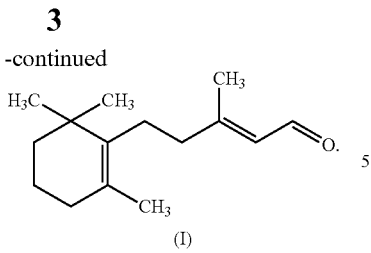

(I)

The rearrangement of step (2) is a Meyer-Schuster rearrangement.

The Meyer-Schuster rearrangement, which was published first in 1922 by Kurt Meyer and Kurt Schuster, is the chemical reaction described as an acid-catalyzed rearrangement of secondary and tertiary propargyl alcohols to α,β-unsaturated aldehydes Therefore the present invention relates to a process (P) for the production of a compound of formula (I) wherein the process comprises as a first step an ethynylation of the compound of formula (III)

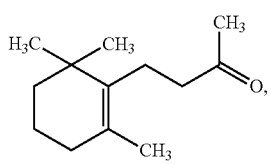

(III)

and as a second step a Meyer-Schuster rearrangement.

As stated above this new way of producing allows to produce 7,8-dihydro-$C_{15}$-aldehyde in a two step-process (instead using the prior art three step-process). The new process has significant advantages over the process known from the prior art:
  Higher space-time-yield
  less energy costs
  improved yield of 7,8-dihydro-$C_{15}$-aldehyde
  easy purification The present invention also relates to a preferred embodiment of the process wherein both steps are carried out by using catalytic process. Such a process has additionally the following advantages:
  fully catalytic process (both steps)
  less waste than in the prior art (especially in step 1), because no stoichiometric amounts of reagents are used!

In the following the two steps of the process according to the present invention are discussed in more detail.

Ethynylation Step (Step (1)):

The starting material is dihydro-β-ionone (compound of formula (III)), which is ethynylated to the compound of formula (VII))

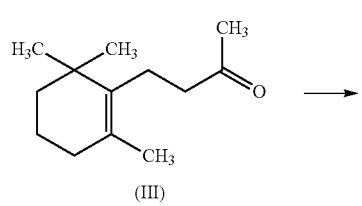

(III)

-continued

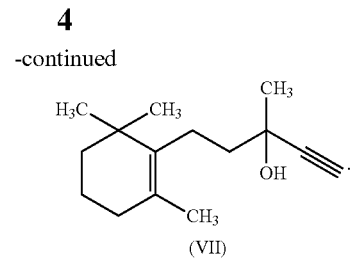

(VII)

This ethynylation can be carried by commonly known processes.

For example the ethynylation can be carried out by a Grignard reaction which is widely used.

Therefore the present invention relates to process ($P_1$), which is process (P), wherein step (1) is a Grignard reaction.

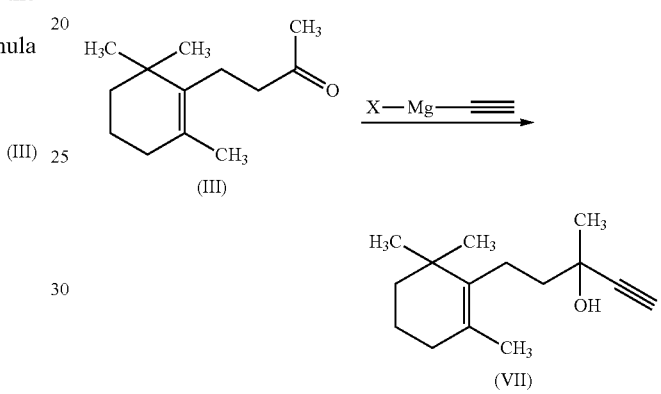

The reaction conditions for the ethynylation by a Grignard reaction are the typical reaction conditions for such well known processes.

Usually Grignard reactions are conducted in anhydrous solvents, especially in ethereal solvents, especially in diethyl ether or in THF.

The Grignard reactant which is used for the ethynylation is the following

X—Mg—≡ wherein

X is a halogen, preferably Br.

This Grignard reactant can either be produced (via the reaction of alkyl magnesium halide with ethyne) or it can be bought commercially.

The Grignard reaction is usually carried out at low temperatures.

After the reaction is completed the product obtained (compound of formula (VII)) is usually purified before used in step (2).

As stated above the ethynylation reaction can also be carried out by using a catalytic reaction step.

Therefore the present invention relates to process ($P_2$), which is process (P), wherein step (1) is carried out by a catalytic reaction step.

A preferred catalytic ethynylation is the one represented by the following scheme:

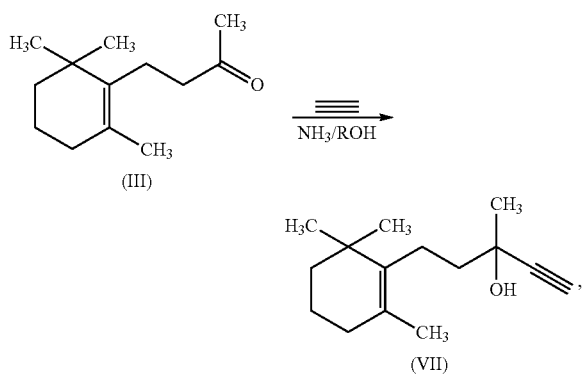

(III) → (VII)

wherein R is K or Cs.

Therefore the present invention relates to process (P$_2$'), which is process (P$_2$), characterized by the following reaction scheme

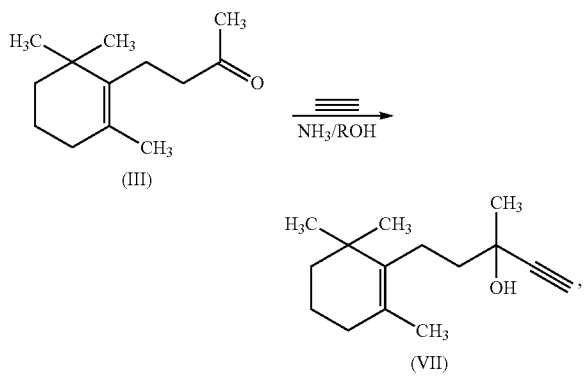

(III) → (VII)

wherein R is K or Cs.

The process (P$_2$') is carried out under pressure. The pressure is in the range from 2 bar to 15 bar, preferably from 5 bar to 12 bar, more preferably from 6 bar to 10 bar.

Therefore the present invention relates to process (P$_3$), which is process (P$_2$'), wherein the pressure is in the range from 2 bar to 15 bar (preferably from 5 bar to 12 bar, more preferably from 6 bar to 10 bar).

The process (P$_2$') is usually carried at a reaction temperature of between −40° C.-10° C., preferably −30°-5° C.

Therefore the present invention relates to process (P$_4$), which is process (P$_2$') or (P$_3$), wherein the process is carried at a reaction temperature of between −40° C.-10° C. (preferably −30°-5° C.)

The process (P$_2$') is usually is carried out in a suitable solvent, usually in NH$_3$ or a similar base.

Therefore the present invention relates to process (P$_5$), which is process (P$_2$'), (P$_3$) or (P$_4$), wherein the process is carried out in NH$_3$.

The ethynylation can also be carried out by other suitable processes.

Meyer-Schuster Rearrangement (Step (2)):

The second step, which follows Step (1), is a Meyer-Schuster rearrangement.

The following scheme illustrates the Meyer-Schuster rearrangement:

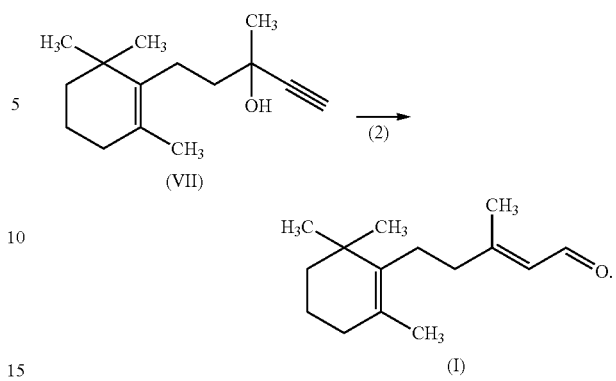

(VII) → (I)

Preferred is a Meyer-Schuster rearrangement using transition metal-based catalysts.

Therefore the present invention relates to a process (P$_6$), which is process (P), (P$_1$), (P$_2$), (P$_2$'), (P$_3$), (P$_4$) or (P$_5$), wherein in the step (2) the rearrangement is carried out by using at least on transition metal-based catalyst.

A preferred embodiment of the present invention relates to a process, wherein the rearrangement is carried out by using at least one Vanadium-based catalyst. It is preferred a vanadate) (such as tris(triphenylsilyl)(V) vanadate), which is used.

Therefore the present invention relates to a process (P$_7$), which is process (P), (P$_1$), (P$_2$), (P$_2$'), (P$_3$), (P$_4$), (P$_5$) or (P$_6$), wherein in the step (2) the rearrangement is carried out by using at least one Vanadium-based catalyst (preferably by using a vanadate).

The substrate (starting material) to catalyst ratio, which is mol-based, in the rearrangement is usually from 5000:1 to 10:1, preferably from 1000:1 to 20:1.

Therefore the present invention relates to a process (P$_8$), which is process (P), (P$_1$), (P$_2$), (P$_2$'), (P$_3$), (P$_4$), (P$_5$), (P$_6$) or (P$_7$), wherein the substrate to catalyst ratio (mol-based) in the rearrangement process (step (2)) is from 5000:1 to 10:1, preferably from 1000:1 to 20:1.

The process according to the present invention is a Meyer-Schuster rearrangement. Mild reaction conditions are used for the process according to the present invention.

Usually the process according to the present invention is carried out in at least one non polar aprotic organic solvent and in the presence of at least one organic acid having a pK value in the range of about 4.0 to about 6.5.

All reactants are added together and mixed. The reaction mixture is heated to the temperature at which the transition metal-based catalytic rearrangement reaction occurs, to provide a resulting mixture.

As organic acids having a pK value in the range of about 4.0 to about 6.5 there come into consideration, inter alia, optionally halogenated, saturated and unsaturated aliphatic carboxylic acids, e.g. acetic acid (pK value 4.74), propionic acid (4.87), chloropropionic acid (3.98) and pivalic acid (5.01) or acrylic acid (4.25); alkanedicarboxylic acids, e.g. adipic acid (4.40); aryl-substituted alkanecarboxylic acids, e.g. phenylacetic acid (4.25); as well as aromatic carboxylic acids, e.g. benzoic acid (4.19) and 4-tert.butyl-benzoic acid (6.50).

The organic acids having a pK value in the range of about 4.0 to about 6.5 are added in at least equimolar amount in regard to the starting material (compound of formula (VII)).

The reaction mixture is usually acidified after the first step has finished to react (usually after a few hours). The acidification step can be carried by using commonly known acids, such as for example sulphuric acid.

As solvents there can be used in the scope of the present invention in general non polar or polar aprotic organic solvents, especially aliphatic, cyclic and aromatic hydrocarbons, such as, for example, $C_7$-$C_{10}$-alkanes, $C_5$-$C_7$-cycloalkanes, benzene, toluene and naphthalene as well as mixtures of such solvents with one another, e.g. paraffin oil (a mixture of saturated aliphatic hydrocarbons); as well as carboxylate esters, such as ethyl acetate.

The rearrangement according to present invention usually comprises two steps:
(1) the rearrangement process is started with the addition of the starting material, the catalyst, the solvent as well as the organic acid having a pK value in the range of about 4.0 to about 6.5 (the sequence of adding these compounds is not of importance. Furthermore it is clear that it is also possible adding mixtures of each of the components as well.)
(2) and optionally afterward the reaction mixture is acidified with an acid or a mixture of acids (such as i.e. sulphuric acid).

Therefore the present invention relates to a process ($P_9$), which is process (P), ($P_1$), ($P_2$), ($P_2'$), ($P_3$), ($P_4$), ($P_5$), ($P_6$), ($P_7$) or ($P_8$), wherein in the rearrangement is carried out in at least one non polar aprotic organic solvent in the presence of at least one organic acid having a pK value in the range of about 4.0 to about 6.5.

Therefore the present invention also relates to a process ($P_9'$), which is process ($P_9$), wherein the organic acid is chosen from the group consisting of acetic acid, propionic acid, chloropropionic acid, pivalic acid, acrylic acid, adipic acid, phenylacetic acid, benzoic acid and 4-tert.butyl-benzoic acid.

Therefore the present invention also relates to a process ($P_9''$), which is process ($P_9$) or ($P_9'$), wherein the organic acid is added in at least equimolar amount in regard to the starting material (compound of formula (II)).

Therefore the present invention also relates to a process ($P_9'''$), which is process ($P_9$), ($P_9'$) or ($P_9''$), wherein the non polar or polar aprotic organic solvent is chosen from the group consisting of aliphatic, cyclic and aromatic hydrocarbons (such as $C_7$-$C_{10}$-alkanes, $C_5$-$C_7$-cycloalkanes, benzene, toluene naphthalene, paraffin oil) and carboxylate esters (such as ethyl acetate).

The rearrangement (step (2)) is usually carried out under very mild reaction condition. The reaction temperature is usually between 10° C. and 50° C. Preferably between 20° and 40° C.

Therefore the present invention relates to a process ($P_{10}$), which is process (P), ($P_1$), ($P_2$), ($P_2'$), ($P_3$), ($P_4$), ($P_5$), ($P_6$), ($P_7$), ($P_8$), ($P_9$), ($P_9'$), ($P_9''$) or ($P_9'''$), wherein the process is carried out at a reaction temperature of 10° C. to 50° C., preferably 20° C. to 40° C.

The following Example illustrates the invention further without limiting it. All percentages and parts, which are given, are related to the weight and the temperatures are given in ° C., when not otherwise stated.

EXAMPLES

Example 1a (Step 1)

Ethynylation of 7,8-dihydro-β-ionone Via Grignard Reaction

In a 350 ml flask flushed with argon, 6.48 g (30.0 mmol) of dihydro-β-ionone was dissolved in 130 ml of anhydrous tetrahydrofuran at 24° C. The solution was cooled to −65° C. to −75° C. Within 20 min 88.5 ml (44.25 mmol) of a 0.5 M solution of ethynyl magnesium bromide in THF were added drop-wise. After complete addition, the cooling bath was removed and the pale yellow solution was allowed to warm to room temperature. After 1 hour at 24° C. the reaction was complete and 50 ml of a saturated ammonium chloride solution was added. After stirring for another 15 min the pale yellow solution was transferred to a separation funnel, diluted with 100 ml of n-hexane, and subsequently washed with saturated sodium bicarbonate solution (1×100 ml), dist. water (2×100 ml) and brine (1×100 ml). The aqueous layers were re-extracted with 100 ml of n-hexane. The combined organic layers were dried over sodium sulfate, concentrated at 35° C. under reduced pressure, and the crude product was purified by column chromatography. The purified product was obtained as pale yellow oil in 82% yield and 84.5% purity.

Example 1b (Step 1)

Catalytic Ethynylation of 7,8-dihydro-β-ionone with Acetylene in $NH_3$/KOH

A 2-liter autoclave was set under nitrogen atmosphere. 680 g (39.93 mol) of ammonia were added and cooled to 0° C. With stirring the autoclave was pressurized with acetylene to 8.06 bara. Then 15 ml of an aqueous KOH solution (44%) were added drop wise. After complete addition of the KOH solution, 354.45 g (1.766 mol, 96.8% purity of 7,8-dihydro-β-ionone were added drop wise. With addition of the ketone the reaction started. When the addition of 7,8-dihydro-β-ionone was finished, another 15 ml of a KOH solution (44%) were added. After 2 hours the reaction mixture was diluted with 200 ml of toluene and the ammonia was released. At 0° C. (0 barg), the reaction mixture was transferred from the reactor into a flask. The reactor was rinsed with 200 ml of toluene, which was also added to the flask.

From the combined mixture the solid KOH was removed at 10° C. by filtration. After that the liquid layer was diluted with 500 ml of water. Also at 10° C. the biphasic mixture was adjusted to pH 7.0 by slow addition of acetic acid (50%). The layers were separated and the aqueous layer was extracted with toluene. The combined organic phases were dried over sodium sulfate, filtered and concentrated under reduced pressure. The crude product was obtained in 85.97% purity (qNMR) and 95.7% yield.

Example 2 (Step 2)

Meyer-Schuster Rearrangement of 7,8-dihydroethynol (3-methyl-5-(2,6,6-trimethylcyclohex-1-enyl) pent-1-yn-3-ol In a 1-liter flask with magnetic stir bar and condenser, 105.4 g (440.5 mmol) of crude 7,8-dihydroethynol (92.1% purity) were dissolved under argon atmosphere in 450 ml of xylene. With stirring, subsequently 12.29 g (13.76 mmol, 3.1 mol %) of tris(triphenylsilyl)(V) vanadate and 897 mg (7.31 mmol, 1.7 mol %) of benzoic acid were added and the light-brown solution was heated to reflux in an oil bath. After stirring at this temperature for 4 hours, the solution was concentrated on a rotary evaporator at reduced pressure and 50° C. water-bath temperature. The crude product was obtained as dark-brown suspension in 82% yield (125.14 g, 63.5% purity) and purified by column chromatography.

(E/Z)-3-methyl-5-(2,6,6-trimethylcyclohex-1-enyl)pent-2-enal was obtained in 78% yield (81.9 g) and 92.63% purity.

The invention claimed is:

1. A process for producing a compound of formula (I):

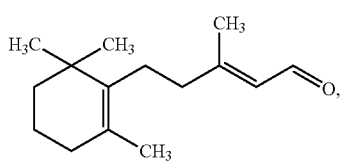

wherein
the process comprises the steps of:
(1) conducting ethynylation of a compound of formula (III):

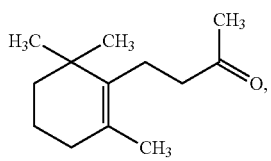

and
(2) performing a Meyer-Schuster rearrangement of the ethynylated compound of formula (III) to obtain the compound of formula (I), wherein
step (1) is carried out by either a Grignard reaction or a catalytic reaction.

2. The process according to claim 1, wherein the ethynylation of step (1) is carried out according to the as following reaction scheme in the presence of $NH_3$ as a solvent:

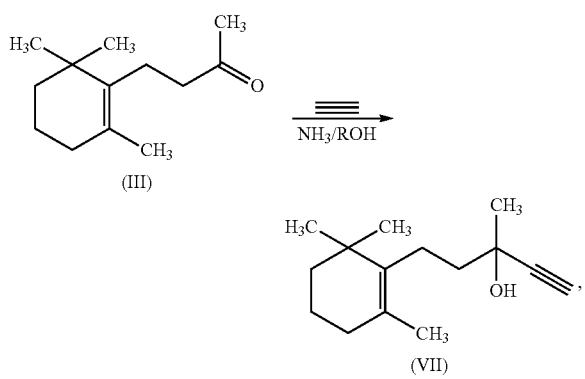

wherein R is K or Cs.

3. The process according to claim 1, wherein step (2) is practiced at a pressure which is in a range from 2 bar to 15 bar.

4. The process according to claim 1, wherein step (2) is practiced at a reaction temperature which is between −40° C.-10° C.

5. The process according to claim 1, wherein the rearrangement of step (2) is carried out by using at least one transition metal-based catalyst.

6. The process according to claim 5, wherein the rearrangement of step (2) is carried out by using at least one Vanadium-based catalyst.

7. The process according claim 5, wherein the at least one transition melt-based catalyst has a substrate to catalyst ratio from 5000:1 to 10:1.

8. A process for producing a compound of formula (I):

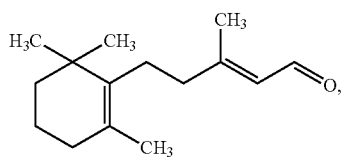

wherein
the process comprises the steps of:
(1) conducting an ethynylation of a compound of formula (III):

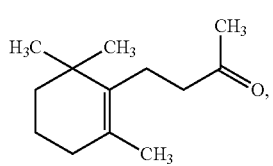

and
(2) performing a Meyer-Schuster rearrangement of the ethynylated compound of formula (III) to obtain the compound of formula (I), wherein
the rearrangement of step (2) is carried out in at least one non-polar or polar aprotic organic solvent in the presence of at least one organic acid having a pK value in the range of about 4.0 to about 6.5.

9. The process according to claim 8, wherein the non-polar or polar aprotic organic solvent is selected from the group consisting of aliphatic hydrocarbons, cyclic hydrocarbons, aromatic hydrocarbons and carboxylate esters.

10. The process according to claim 8, wherein the organic acid is selected from the group consisting of acetic acid, propionic acid, chloropropionic acid, pivalic acid, acrylic acid, adipic acid, phenylacetic acid, benzoic acid and 4-tert-.butyl-benzoic acid.

11. The process according to claim 1, wherein the rearrangement of step (2) is carried out at a reaction temperature of 10° C. to 50° C.

12. The process according to claim 1, wherein the rearrangement of step (2) is carried out at a reaction temperature of 20° C. to 40° C.

13. The process according to claim 8, wherein the non-polar or polar aprotic organic solvent is selected from the group consisting of $C_7$-$C_{10}$-alkanes, $C_5$-$C_7$-cycloalkanes, benzene, toluene, naphthalene, paraffin oil and ethyl acetate.

14. The process according claim 7, wherein the substrate to catalyst ratio is from 1000:1 to 20:1.

* * * * *